United States Patent [19]

Leach

[11] 4,056,385
[45] Nov. 1, 1977

[54] ALANINE DERIVATIVES AS SUGAR CANE RIPENERS

[75] Inventor: Ronald W. A. Leach, Sittingbourne, England

[73] Assignee: Shell Oil Company, Houston, Tex.

[21] Appl. No.: 742,320

[22] Filed: Nov. 16, 1976

[30] Foreign Application Priority Data

Nov. 27, 1975 United Kingdom ............... 48796/75

[51] Int. Cl.² ............................................. A01N 9/20
[52] U.S. Cl. ...................................... 71/111; 71/115; 71/76
[58] Field of Search ............................ 71/111, 115, 76

[56] References Cited

U.S. PATENT DOCUMENTS

| 3,598,859 | 8/1971 | Yates et al. | 71/115 |
| 3,761,508 | 9/1973 | Haddock | 71/115 |

Primary Examiner—Lewis Gotts
Assistant Examiner—Catherine L. Mills

[57] ABSTRACT

Sugar cane is ripened by treatment of the growing plants with certain alanine derivatives.

1 Claim, No Drawings

ALANINE DERIVATIVES AS SUGAR CANE RIPENERS

BACKGROUND OF THE INVENTION

Sugar cane is said to be "ripe" for harvesting when the sugar concentration within the cane reaches its peak. Processing facilities at sugar cane mills are naturally limited and very often have to process cane which is not at peak ripeness. It follows, therefore that if peak ripeness in cane sugar could be artificially induced or maintained at its peak for a longer period of time, yields per hectare would be increased and, moreover, it would lead to more efficient use of mill capacity.

DESCRIPTION OF THE INVENTION

A family of compounds has been found which has the property of ripening sugar cane and, accordingly, the present invention provides a method for effecting ripening of sugar cane which comprises applying to the growing plant, in an amount which induces ripening of the cane, a compound of the following formula:

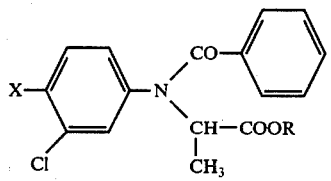

wherein X is chlorine or fluorine and R is hydrogen, an alkyl group containing 1 to 6 carbon atoms, for example methyl, ethyl or isopropyl, or an alkali metal, alkaline earth metal, ammonium or alkyl-substituted ammonium ion.

Examples of this family of compounds which can be used as sugar cane ripeners are:
ethyl N-benzoyl-N-(3,4-dichlorophenyl)-2-aminopropionate N-benzoyl-N-(3,4-dichlorophenyl)-2-aminopropionic acid sodium N-benzoyl-N-(3,4-dichlorophenyl)-2-aminopropionate dimethylammonium N-benzoyl-N-(3,4-dichlorophenyl)-2-aminopropionate N-benzoyl-N-(3-chloro-4-fluorophenyl)-2-aminopropionic acid methyl N-benzoyl-N-(3-chloro-4-fluorophenyl)-2-aminopropionate ethyl N-benzoyl-N-(3-chloro-4-fluorophenyl)-2-aminopropionate isopropyl N-benzoyl-N-(3-chloro-4-fluorophenyl)-2-aminopropionate The time of application of the compound depends much on the prevailing climatic conditions and the load capacity of nearby sugar mills but, generally speaking, efficient results are obtained when the ripener is applied to the cane 5 to 9 weeks before normal harvesting of the cane. Alternatively, in order to spread further the processing loads on sugar cane mills, the peak ripeness period may be prolonged by applying the compound to the sugar cane 2 to 5 weeks after the time at which peak sugar concentration in the cane has been reached.

The dosage of the compound applied to the cane may be in the range 0.5 to 7 kilograms per hectare, preferably in the range 1 to 4 kilograms per hectare.

In the sugar cane industry, the term "sugar cane ripener" is used to mea a substance which not only increases the sugar yield from harvested cane, but also maintains the sugar content at its peak for a longer period of time than is experienced with untreated sugar cane. This means that the ripener can be applied to the cane before and/or after the typical peak sugar concentration in the cane has been reached.

The ripener may be applied to the cane as such, but as is normal practice in the application of chemicals to plants, it is preferred to apply the ripener in the form of a composition which in addition to the ripener also comprises a carrier or a surface-active agent or both a carrier and a surface-active agent.

The term "carrier" as used herein means a material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually employed in formulating herbicides may b used as the carrier.

Suitable solid carriers are natural and synthetic clays and silicates for example, talcs; magnesium aluminium silicates, for example, attapulgites and vermiculties; aluminium silicates, for example, kaolinites, montmorillonites and micas; calcium carbonates; calcium sulphate; synthetic hydrated silicon oxides and synthetic calcium or aluminium silicates; elements such as for example, carbon and sulphur; natural and synthetic resins such as for example, coumarone resins, polyvinyl chloride and styrene polymers and copolymers; solid polychlorophenols; bitumen; waxes such as for example, beeswax, paraffin wax, and chlorinated mineral waxes; and solid fertilizers, for example superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine, light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose of pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates of sulphonates of these condensation products; alkali or alkaline earth metal salts, preferably sodium salts, of sulphuric or sulphuric acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% w of toxicant and usually contain, in addition to solid carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder, but without a dispersant, and are diluted in the field with further solid carrier to give a composition usually containing ½–10% w of toxicant. Granules are usually prepared to have a size between 10 and 100 BS mesh, and may be manufactured by agglomeration or impregnation techniques. Generally, granules will contain ½–25% w toxicant and 0–10% w of additives such as stabilizers, slow release modifiers and binding agents. Emulsifiable concentrates usually contain, in addition to the solvent and, when necessary, co-solvent, 10–50% w/v toxicant, 2–20% w/v emulsifiers and 0–20% w/v of appropriate additives such as stabilizers, penetrants and corrosion inhibitors. Suspension concentrates are compounded so as to obtain a stable, non-sedimenting, flowable product and usually contain 10–75% w toxicant, 0.5–15% w of dispersing agents, 0.1–10% w of suspending agents such as protective colloids and thixotropic agents, 0–10% w of appropriate additives such as defoamers, corrosion inhibitors, stabilisers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

The compositions of the invention may contain other ingredients, for example, protective colloids such as gelatin, glue, casein, gums, cellulose ethers, and polyvinyl alcohol; thixotropic agents e.g. bentonites, sodium polyphosphates; stabilisers such as ethylene diamine tetra-acetic acid, urea, triphenyl phosphate; other herbicides or pesticides; and stickers, for example, non-volatile oils.

Aqueous dispersion and emulsions, for example, compositions obtained by diluting a wettable powder or an emulsifiable concentrate according to the invention with water, also lie within the scope of the present invention. The said emulsions may be of the water-in-oil or of the oil-in-water type, and may have a thick "mayonnaise"-like consistency.

The invention is further illustrated in the following Example:

EXAMPLE

A series of tests were carried out at Trinidad using an existing bed of sugar cane about 12 months old. Plots of sugar cane were formed by cutting walkways through the crops and extra or abnormal tillers were removed prior to treatment. The compounds as well as the formulations employed are given in Table I and were sprayed on the plants using an overhead sprayer. Three replicates of each treatment were carried out.

Samplings were made at 4 and 6 weeks after treatment which took place in August at a time when the Tc/Ts ratio of the harvested cane was increasing, that is to say when the canes were losing their sucrose content and were on the decline phase of ripening. The ratio Tc/Ts is defined as the figure obtained by dividing the tonnage of harvested sugar cane by the tonnage of sucrose content in the harvested cane and it will be seen that this figure decreases as the sugar yield increases and vice versa.

The results of these tests in terms of the Tc/Ts ratio for each compound is shown in Table II.

TABLE I

| Compound | X | R | Formulation |
|---|---|---|---|
| A | Cl | $C_2H_5$ | 20% E.C. diluted with water |
| B | F | $C_2H_5$ | 12.5% E.C. diluted with water |
| C | F | H | 15% aqueous solution of sodium salt |
| D | F | $CH_3$ | 15% E.C. diluted with water |

E.C. = emulsifiable concentrate

TABLE II

| | | Tc/Ts ratio at harvesting | |
|---|---|---|---|
| Compound | Dose Rate kg/ha | 4 weeks after treatment | 6 weeks after treatment |
| A | 2.00 | 12.1 | 12.2 |
| B | 0.75 | 12.8 | 12.7 |
| C | 2.00 | 14.0 | 13.3 |
| D | 2.00 | 13.3 | 13.7 |
| Control | — | 14.00 | 14.8 |

It will be seen from the above Table II that 6 weeks after treatment the sucrose yield for all the compounds is higher than in the case of the untreated control. With the exception of Compound C all the compounds also give rise to increases in sucrose yields when harvesting is effected 4 weeks after treatment.

I claim:

1. A method for effecting ripening of sugar cane which comprises applying to the growing plant an effective amount of a compound of the formula:

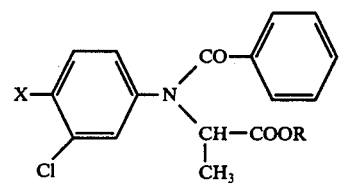

wherein X is chlorine or fluorine and R is hydrogen, an alkyl group containing 1 to 6 carbon atoms, or an alkali metal, alkaline earth metal, ammoniuum or alkyl-substituted ammonium ion.

* * * * *